United States Patent [19]
Teeter

[11] Patent Number: 5,047,403
[45] Date of Patent: Sep. 10, 1991

[54] METHOD FOR THE REDUCTION OF HEAT DISTRESS INDUCED NICARBAZIN TOXICITY IN FOWL

[76] Inventor: Robert G. Teeter, 4814 Country Club Ct., Stillwater, Okla. 74074

[21] Appl. No.: 396,194

[22] Filed: Aug. 21, 1989

[51] Int. Cl.$^5$ ................... A61K 31/54; A61K 31/505
[52] U.S. Cl. ................................ 514/224.8; 514/256
[58] Field of Search ............... 514/256, 224.8; 544/36

[56] References Cited

U.S. PATENT DOCUMENTS

| 2,415,363 | 6/1944 | Mitchell et al. | 544/36 |
| 2,428,444 | 10/1947 | Whiting | 514/224.8 |
| 2,731,382 | 1/1956 | Basso et al. | 514/274 |
| 2,731,383 | 1/1956 | O'Neill et al. | 514/596 |
| 2,731,384 | 1/1956 | O'Neill et al. | 514/345 |
| 2,840,504 | 6/1958 | Vierling | 514/224.8 |
| 3,591,692 | 7/1971 | Sutton | 514/224.8 |
| 4,729,894 | 3/1988 | Teeter | 424/679 |

OTHER PUBLICATIONS

Chemical Abstracts (110:63742d), 1989.
Chemical Abstracts (100:17255t), 1984.
Chemical Abstracts (97:161192g), 1982.
Fuller et al., *Proc. Maryland Nutr. Conf.*, pp. 58–64 (1973).
Waldroup et al, *Poultry Sci.*, 55, pp. 243–253 (1976).
Squibb et al, *Poultry Sci.*, 38, pp. 220–221 (1959).
Smith et al, *Poultry Sci.*, 62, 1504, Absts. (1983).

*Primary Examiner*—Frederick E. Waddell
*Assistant Examiner*—Kevin E. Weddington
*Attorney, Agent, or Firm*—David L. Rose; Joseph F. DePrima

[57] ABSTRACT

There is disclosed a method for the reduction of a toxicity resulting from the use of nicarbazin in fowl during periods of high heat distress. The method involves the administration of phenothiazine during periods of high ambient temperature and/or relative humidity which are concurrent with periods of nicarbabin treatment. The use of phenothiazine during periods of potential heat induced toxicity caused by the administration of nicarbazin results in reduced mortality, higher feed efficiency and higher weight gain than is observed without the use of phenothiazine.

17 Claims, No Drawings

METHOD FOR THE REDUCTION OF HEAT DISTRESS INDUCED NICARBAZIN TOXICITY IN FOWL

BACKGROUND OF THE INVENTION

It is generally known that poultry such as chickens, geese, turkeys, quail, pheasants and the like are particularly susceptible to poor productivity (reduced growth rate, feed efficiency, egg shell quality and high mortality) during periods of environmental heat distress (high ambient temperatures and high relative humidity). It is also generally well known that these heat distress effects are greatly exacerbated if the anticoccidial agent nicarbazin (Nicarb) is administered during such heat distress periods.

Heat distress substantially reduces the growth rate of broiler chicks. Diets have been altered to reduce this problem via reducing the heat increment of the diet with fat supplementation (H. L. Fuller et al; "Effect of Heat Increment of the Diet on Feed Intake and Growth of Chicks Under Heat Stress", *Proc. Maryland Nutr. Conf.*, pp 58–664, 1973) and improved the amino acid balance (P. W. Waldroup et al; "Performance of Chicks Fed Diets Formulated to Minimize Excess Levels of Essential Amino Acids", *Poultry Sci.*, 55:243–253, 1976). It has also been suggested that the decline in growth rate results directly from reduced feed intake (R. L. Squibb et al; "Growth and Blood Constitutients of Immature New Hampshire Fowl Exposed to Constant Temperatures of 99° C. for 7 Days", *Poultry Sci.*, 38:220–221, 1959). It has been demonstrated that the growth rate of heat stressed broilers can be increased by force feeding at a level exceeding ad libitum feed intake (M. O. Smith et al; "Feed Intake and Environmental Temperature Effects Upon Growth, Carcass Traits, Ration Digestibility, Digestive, Passage Rate and Plasma Parameters in *Ad Libitum* and Force-Fed Broiler Chicks" *Poultry Sci.*, 62:1504 abstr., 1983).

SUMMARY OF THE INVENTION

This invention is concerned with the alleviation of heat distress symptoms and mortality which occur with the administration of nicarbazin to poultry. More particularly, this invention is concerned with the administration of phenothiazine to poultry which are also being administered nicarbazin during periods of heat distress in order to eliminate the toxicity caused by the combination of heat distress and nicarbazin. Thus, it is an object of this invention to describe such a method to reduce these effects. A further object is to describe the feed and water compositions containing nicarbazin and phenothiazine for administration to poultry. A still further object is to describe the amounts of penothiazine and nicarbazin which are found in the feed and water compositions used for the administration of the drugs. Further objects will become apparent from a reading of the following description.

DESCRIPTION OF THE INVENTION

It has been unexpectedly discovered that the well known toxic effects of nicarbazin upon poultry subject to heat distress, that is prolonged periods of high ambient temperature and/or relative humidity, can be alleviated or eliminated if phenothiazine, a known insecticide and anthelmintic agent, is administered during the period of nicarbazin treatment which occurs during periods of heat distress. The typical symptoms of nicarbazin heat distress toxicity of reduced weight gain, reduced feed effiency and death are all significantly reduced when phenothiazine is used to counteract nicarbazin heat distress toxicity.

The toxic effects of nicarbazin will begin to be observed during summertime conditions when the daily high temperature, as measured inside the poultry building, exceeds 28° C. The toxic effects of the combination of high temperature, humidity and nicarbazin will vary with age of the bird, the genetic make-up and the previous exposure of the bird to high temperatures. A brief exposure to temperatures in excess of 30° C. may have only a moderate toxic effect upon the bird while a longer exposure at 28° C. could have a more severe effect. The method of this invention will reduce the heat induced toxicity in both cases. Since poultry will generally rely on the mechanism of panting to help dissipate body heat, higher levels of relative humidity will reduce the efficiency of panting as a cooling mechanism and will increase the toxic effect of nicarbazin/heat distress combination.

Nicarbazin is generally administered to poultry such as chickens, geese, turkeys, ducks, quail, pheasant, and the like at levels of from 100 to 150 ppm in the feed, preferably about 125 ppm. Because it is highly insoluble in water, nicarbazin is generally not administered in poultry drinking water.

When phenothiazine is added to the poultry feed in amounts of from 160 to 10,000 ppm under heat stress conditions, the toxic effects of nicarbazin were completely reversed and phenothiazine tested birds were essentially indistinguishable from the control birds. Preferably the phenothiazine is administered at from 160 to 625 ppm and most preferably at about 320 ppm.

Phenothiazine, being a basic compound, is capable of forming pharmaceutically acceptable acid addition salts with increased water solubility. Thus, the phenothiazine can also be readily administered as a part of the poultry drinking water. The phenothiazine is generally administered in the water ration at levels of from 50 to 1000 ppm. Preferably the phenothiazine is administered at from 100 to 500 ppm and most preferably at about 250 to 300 ppm.

The preferred acid addition salts of phenothiazine are those derived from hydrohalic acids, preferably hydrochloric, or other mineral acids such as nitric, sulfuric, phosphoric and the like. Organic acids such as acetic acid are also suitable.

Specifically, tests were carried out wherein chickens were subjected to temperatures with a daily variation of from 24° to 35° C. with temperatures exceeding 32° C. for about 6 hours per day. In addition, the relative humidity was maintained at from 35 to 50%. In such tests, nicarbazin was administered at 0 (control) and 125 ppm and phenothiazine was administered at from 0 to 2500 ppm. The addition of nicarbazin decreased the number of birds surviving the study by 47%; decreased the weight gain by 19%; and decreased feed efficiency by 47%. The addition of phenothiazine at all doses of about 160 ppm and higher, produced survivability, weight gain and feed effiency which were indistinguishable from the control birds.

The compounds of this invention are orally administered to poultry for the control of nicarbazin induced heat stress. Any number of conventional methods are suitable for administering the compounds of this invention to poultry, as for example, they may be given in the poultry feed.

Of the various methods of administering the compounds of this invention to poultry, they are most conveniently administered as a component of a feed composition. The novel compounds may be readily dispersed by mechanically mixing the same in finely ground form with the poultry feedstuff, or with an intermediate formulation (premix) that is subsequently blended with other components to prepare the final poultry feedstuff that is fed to the poultry. Typical components of poultry feedstuffs include molasses, fermentation residues, corn meal, soybean meal, fish meal, ground and rolled oats, wheat shorts and middlings, alfafa, clover and meat scraps, together with mineral supplements such as bone meal and calcium carbonate and vitamins and amino acid supplementation.

The following examples are provided that the invention might be more fully understood. They should not be contrued as limitations of the inventions.

EXAMPLE 1

Trials utilizing 1920 birds have been conducted according to the following protocol. Nicarbazin (125 ppm) addition to the basal ration decreased ($P<0.01$) live weight gain (18.6%), survivability (47%), and feed efficiency (47%). Feed efficiency values were reduced by nicarbazin primarily as a result of its effect upon mortality. Phenothiazine addition (312.5, 625, 1250, 2500 ppm) to nicarbazin containing rations returned ($P>0.1$) all production parameters (gain, survival, feed efficiency) to control values. No difference was detected ($P>0.1$) between the 312.5 ppm and the 2500 ppm phenothiazine levels for any of the parameters evaluated.

Phenothiazine was tested for efficacy to ameliorate nicarbazin toxicity according to the following treatments.

| TRT. | Nicarbazin (ppm) | Phenothiazine (ppm) |
| --- | --- | --- |
| Control | 0 | 0 |
| 1 | 125 | 0 |
| 2 | 125 | 312.5 |
| 3 | 125 | 625 |
| 4 | 125 | 1250 |
| 5 | 125 | 2500 |

Birds were allotted to treatment such that individual treatment groups contained 16 replicates of 6 chicks per replicate.

Environment: The enviromental chamber was set to oscillate between 24° C. and 35° C. in a manner simulating a typical summer day. Hours in excess of 32° C. averaged approximately 6 hours per day. Relative humidity was maintained between 35 and 50%.

Parameters/Statistical Analysis: Parameters monitored included live weight gain, feed consumption, water consumption, feed efficiency and mortality. Live weight gain was estimated by the difference between initial and final body weights. Feed consumption was recorded for each replicate while water consumption was tallied over 8 replicates within a treatment group (2 observations/trt). Feed efficiency was estimated by dividing total weight of birds surviving the study in each replicate by the total feed consumed. No effort was made to adjust feed efficiency for mortality as it was anticipated that the mortality effects on feed efficiency would be significant, adversely affected by treatment and of economic importance to the poultry industry. All data were subjected to analysis of variance using the General Linear Model of the statistical analysis system. When a significant F statistic was indicated by the analysis of variance for treatment, means were separated by least squares analyses utilizing the model which accounted for the greatest variation in the most efficient manner.

OBJECTIVE

The objective of the experiment described herein is to refine the dose titration of 125 ppm nicarbazin with 4 graded levels of phenothiazine.

MATERIALS AND METHODS

Test Animals: Vantress X Arbor Acre male chicks, numbering 1,300 were raised on rice hull litter and fed starter ration during the first 3 weeks posthatching. This pre-experimental time period was necessary in order to bring birds to the age at which they become susceptible to heat distress. On the first day of the $4^{th}$ week, following an overnight fast, 960 chicks were selected at random, weighed and randomly allotted to treatment groups.

| STARTER AND GROWER RATIONS | | |
| --- | --- | --- |
| INGREDIENT | STARTER | GROWER |
| Corn | 53.7 | 56.75 |
| Soybean meal | 40.0 | 36.0 |
| Tallow | 1.8 | 3.0 |
| Dicalcium Phospha | 2.35 | 2.35 |
| Calcium Carbomate | 1.2 | 0.9 |
| Salt | 0.4 | 0.5 |
| Vitamin Supplement | 0.3 | 0.3 |
| Trace Minerals | 0.1 | 0.1 |
| dl-Methionine | 0.15 | 0.1 |
| | 100.0 | 100.0 |

Management: At all times, save for the overnight fast at experiment initiation (4 weeks post-hatching), both feed and water were available for ad libitum consumption. Rations utilized were formulated to provide at least 105% of the requirement for essential nutrients specified by the Nutrient Requirement Council with the exception that energy mimicked current industry standards. The energy standards established by the NRC were used to establish nutrient/calorie ratios.

Test Drugs: The phenothiazine available to the agricultural industry has an $8\mu$ particle size. However, a $3\mu$ particle size is also available by special order and was utilized in this study. The smaller particle size may be more desirable for enhanced absorption and a lowered effective dosage rate.

The addition of nicarbazin to the basal ration decreased ($P<0.01$) survival (40%), live weight gain (27%) and feed efficiency (46%). Survival in this study for chicks receiving nicarbazin in the absence of phenothiazine averaged 40% while survival for heat distressed chicks not fed nicarbazin averaged 92% Nicarbazin effects on live body weight gain have been mixed in other studies with results ranging from no effect to significant reductions. This variation is likely due to the birds previous exposure to heat distress and the severity of the stress encountered. In this study the birds had no prior exposure to heat distress and were subsequently exposed to a significantly elevated ambient temperature with the result that weight gains were reduced by 27%. Feed efficiency for birds consuming the nicarbazin supplemented ration without phenothiazine was reduced (P<0.01) by 46% which is a reflection of both the depressed weight gain and survival. No effort was made to adjust feed efficiency values for mortality, therefore the feed efficiency values are producer oriented.

The phenothiazine by nicarbazin interaction as well as the quadratic effect of phenothiazine within this interaction was significant (P<0.01) for survival, gain and feed efficiency. This interaction may be attributed to the slight effect of phenothiazine on the broiler parameters monitored in contrast to the large phenothiazine effect in the presence of nicarbazin.

Phenothiazine additions (312.5, 625, 1250, and 2500) to the basal ration containing 125 ppm nicarbazin returned all production parameters to control values. No significant differences (P>0.1) were detected between the phenothiazine doses in rations containing nicarbazin for survival, live weight gain and feed efficiency. Phenothiazine addition to the basal ration in the absence of nicarbazin tended (P<0.1) to increase survival at the 1250 ppm supplementation level, but only numerically increased survival at 2500 ppm. Phenothiazine tended (P<0.1) to enhance growth rate in rations without nicarbazin at the 2500 ppm supplementation, level, but only numerically enhanced growth rate at the other levels. Feed efficiency values parallel survival. Averaging phenothiazine supplementation levels over nicarbazin indicated a non-significant F statistic for survival, body weight gain, and feed efficiency.

Conclusion

The capability of phenothiazine to reduce nicarbazin's toxic effects in male broilers during heat distress is sufficient to reduce nicarbazin induced heat stress toxicity to control levels. The lowest effective phenothiazine dose necessary to elicit a maximal response was not detected suggesting that it is equal to or less than 312.5 ppm.

EXAMPLE 2

Summary

One trial utilizing 960 birds was conducted to further refine the dose titration of nicarbazin (125 ppm) with graded phenothiazine levels (0, 80, 160, 320, 640 ppm). All rations evaluated in the study contained nicarbazin. Linear effects of phenothiazine supplementation were significant (P<0.01) as phenothiazine increased survival from 28% for birds consuming ration supplemented with 0 ppm to 60.2% for the 640 ppm supplementation level. The 320 ppm phenothiazine level was similar (P=0.948) to the 640 ppm level with bird survival at 59.9 and 60.2% respectfully. Some signs of toxicity were observed at the 160 ppm dose indicating that the minimal effective dose for full heat distress protection, lies within the 160 and 320 ppm phenothiazine inclusion levels. Results are consistent with Example 1 where the 312.5 and 625 ppm phenothiazine levels were judged similar. Gain was not affected by phenothiazine level (P>0.1) while feed efficiency paralleled bird survival. The high mortality observed in this study occurred on day 4 of the assay when the relative humidity increased to 72% as the result of a defective humidistat. A nicarbazin free control treatment group was not included in this experiment so that treatment replication could be maximized. The data do indicate that phenothiazine has efficacy under extremely stressful environments and that the minimal effective dose is likely between 160 and 320 ppm.

Objective

The purpose of this trial was to further refine the dose titration of 125 ppm nicarbazin with graded levels of phenothiazine in heat distressed broilers.

MATERIALS AND METHODS

Test Animals: Vantress X Arbor Acre male chicks, numbering 1,300, were raised on rice hull litter and fed starter ration during the first 3 weeks posthatching. This time period was necessary to bring birds to the age at which they become susceptible to heat distress. On the first day of the $4^{th}$ week, following an overnight fast, chicks were weighed and randomly allotted to treatment groups.

Management: At all times, save the overnight fast at experiment initiation, both feed and water were available for ad libitum consumption. Rations utilized were formulated to provide at least 105% of the requirement for essential nutrients specified by the Nutrient Requirement Council with the exception that energy mimicked industry standards. The energy standards established by the NRC were used to establish nutrient/calorie ratios.

Test Drug: The phenothiazine marketed to the agricultural industry has an $8\mu$ particle size. However, a $3\mu$ particle size is also available by special order and was utilized in this study. The smaller particle size may be desirable for enhanced absorption and a lowered dosage rate with maximal efficacy.

Treatments and Allocation: Treatment groups consisted of the following nicarbazin-phenothiazine combinations:

| TRT. | Nicarbazin (ppm) | Phenothiazine (ppm) |
| --- | --- | --- |
| 1 | 125 | 0 |
| 2 | 125 | 80 |
| 3 | 125 | 160 |
| 4 | 125 | 320 |
| 5 | 125 | 640 |

Birds were allotted to treatment such that individual treatment groups contained 32 replicates of 6 chicks per replicate. The treatment groups evaluated did not include birds fed a nicarbazin free ration in order that replication could be maximized to separate phenothiazine supplementation levels.

Environment: The environmental chamber was set to oscillate between 24° C. and 35° C. in a manner simulating a typical summer day. Hours in excess of 32° C. averaged approximately 6 hours per day. It was intended that relative humidity be regulated between 45 and 50%. However, on day 4 of the experiment a defective humidistat remained in the "on" position with the result that relative humidity soared to 72%. This high level of relative humidity constituted an extremely acute heat distress environment with the result that mortality was massive. Based upon one previous experience in the environmental chamber where relative humidity rose to over 80% with an ambient temperature of just 31° C., it would be expected that mortality for birds not consuming nicarbazin to also have been dramatically elevated.

Parameters/Statistical Analysis: Parameters monitored included live weight gain, feed consumption, feed efficiency and mortality. Live weight gains were estimated by difference between initial and final body weights. Feed consumption was recorded for each replicate. Feed efficiency was estimated by dividing total weight of birds surviving the study, for each replicate, by the total feed consumed. No effort was made to adjust feed efficiency for mortality as the mortality effects on feed effiency were significant and adversely affected by treatment. All data were subjected to analysis of variance using the General Linear Model of the statistical analysis system. When a significant F statistic was indicated by the anaylsis of variance for treatment, means were separated by least squares analyses utilizing the model which accounted for the greatest variation in the most efficient manner detected.

Discussion

Data collected in this study were consistent with numerous other studies where phenothiazine has been observed to ameliorate nicarbazin toxicity occurring in broilers during heat distress. In contrast to other experiments where the phenothiazine doses evaluated exceeded 300 ppm the linear effects of phenothiazine supplementation were significant ($P<0.01$). Phenothiazine increased survival from 28% for birds consuming ration supplemented with 0 ppm to 60.2% for the 640 ppm supplementation level. The 320 ppm phenothiazine level was similar ($P=0.948$) to the 640 ppm level with bird survival at 59.9 and 60.2% respectfully. Specifically, this observation is consistent with Example 1 where the 312.5 and 625 ppm phenothiazine levels were also judged similar. Survival, however, was some what reduced ($P<0.01$) in this study for the 80 and 160 ppm doses indicating that the minimal effective dose for full heat distress protection likely lies within the 160 and 320 ppm phenothiazine inclusion levels. Gain was not affected by phenothiazine level ($P>0.1$) while feed efficiency paralleled bird survival. The high mortality observed in this study occurred on day 4 of the assay when the relative humidity increased to 72% as the result of a defective humidistat. A nicarbazin free control treatment group was not included in this experiment in order that treatment replication could be maximized. However, based upon previous experience this type of acute heat distress would be expected to also significantly increase the mortality of birds consuming nicarbazin free rations.

Conclusion

Data collected in this study indicate that phenothiazine efficacy under extremely stressful environments and that the minimal effective dose for full heat distress protection is likely within the 160 and 320 ppm levels.

What is claimed is:

1. A method for treating heat distress in poultry induced by the administration of nicarbazin to such poultry during periods of high ambient temperature and/or relative humidity which comprises administering an effective amount of phenothiazine, or a salt thereof, to such poultry during such periods of nicarbazin administration.

2. The method of claim 1 wherein the phenothiazine is orally administered.

3. The method of claim 2 wherein the phenothiazine is administered as a part of the poultry feed or water ration.

4. The method of claim 3 wherein the phenothiazine is administered at from 160 to 10,000 ppm as part of the poultry feed ration.

5. The method of claim 4 wherein the phenothiazine is administered at from 160 to 640 ppm as part of the poultry feed ration.

6. The method of claim 5 wherein the phenothiazine is administered at about 320 ppm is part of the poultry feed ration.

7. The method of claim 3 wherein the phenothiazine is administered at from 50 to 1000 ppm as part of the poultry water ration.

8. The method of claim 7 wherein the phenothiazine is administered at from 100 to 500 ppm as part of the poultry water ration.

9. The method of claim 8 wherein the phenothiazine is administered at from 250 to 300 ppm as part of the poultry water ration.

10. The method of claim 1 wherein the salt of phenothiazine is an acid addition salt.

11. The method of claim 10 wherein the salt of phenothiazine is derived from a mineral acid or an organic acid.

12. The method of claim 11 wherein the mineral acid is hydrohalic, nitric, sulfuric or phosphoric acid.

13. The method of claim 12 wherein the hydrohalic acid is hydrochloric.

14. The method of claim 11 wherein the organic acid is acetic acid.

15. The method of claim 1 wherein the phenothiazine is administered to nicarbazin induced heat stressed poultry when the daily high temperatures of the poultry environment exceeds 28° C.

16. The method of claim 1 wherein the poultry is chickens, geese, turkeys, ducks, quail or pheasants.

17. The method of claim 16 wherein the poultry is chickens.

* * * * *